(12) United States Patent
Brunerie

(10) Patent No.: US 6,384,243 B1
(45) Date of Patent: *May 7, 2002

(54) METHOD FOR PRODUCING NATURAL DIOL-1,3 DERIVATIVES AND CORRESPONDING NATURAL 1,3-DIOXANE DERIVATIVES

(75) Inventor: Pascal Marc Brunerie, Santeny (FR)

(73) Assignee: Pernod Ricard, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,545

(22) PCT Filed: Jul. 15, 1997

(86) PCT No.: PCT/FR97/01309

§ 371 Date: Jan. 19, 1999

§ 102(e) Date: Jan. 19, 1999

(87) PCT Pub. No.: WO98/02428

PCT Pub. Date: Jan. 22, 1998

(30) Foreign Application Priority Data

Jul. 16, 1996 (FR) .............................. 96 08852

(51) Int. Cl.$^7$ ................ C07D 319/06; C07C 27/26
(52) U.S. Cl. ..................... 549/376; 568/869
(58) Field of Search ............ 549/376; 568/869

(56) References Cited

PUBLICATIONS

Yajima et al. Agric. Biol. Chem., 48(4), 849–855 1984.*
Dettweiller et al., Dtsch. Lebensm. Rundsch. 86(6), 174–76 (1990).*

Dettweiler, G. et al, "Occurence of C8–diols in Apple Fruit", Deutche Lebensmittel–Rundschau, 86 Jahrg. Heft 6, 1990, 174–6.

Durr, P. et al, "The Contribution of Some Volatiles to the Sensory Quality of Apple and Orange Juice Odour", Flavour '81, Walter de Gruyter & Co., Berlin 1981, pp. 179–193.

Pyysalo, T. et al, "Volatile Constituents and Odour Quality Of Apple Juice", Ber. Int. Fruchtsaftunion, 1980, 16, S. 343–53.

Schwab, W. et al, "Identification of 3–Hydroxyoctyl β–D–Glucoside and Absolute Configuration of Free and Bound Octane–1,3–Diol in Apple Fruit", Phytochemistry, vol. 28, No. 1, 1989 pp. 157–160.

Yajima, I. et al, "Volatile Flavor Components of Kogyoku Apples", Agric Biol. Chem., 48(4), 1984, pp. 849–855.

Riechstoffe Aromen Korperpflegemittel, vol. 19, No. 4, Apr. 1969, p. 157.

Russian Journal of General Chemistry, vol. 64, No. 10, Oct. 1994, pp. 1555–1556.

The Journal of Physical Chemistry, vol. 88, No. 4, Feb. 16, 1984, pp. 807–809.

* cited by examiner

Primary Examiner—T. A. Solola
(74) Attorney, Agent, or Firm—Jacobson Holman, PLLC

(57) ABSTRACT

An unsaturated fatty acid precursor of a natural 1,3-diol derivative, which precursor is the same as that which is naturally present in a cider apple, is enzymatically converted to the natural 1,3-diol derivative.

24 Claims, 2 Drawing Sheets

METHOD FOR PRODUCING NATURAL DIOL-1,3 DERIVATIVES AND CORRESPONDING NATURAL 1,3-DIOXANE DERIVATIVES

This APPLN. is a 371 of PCT/FR97/01309 filed Jul. 15, 1997

The present invention relates to the production of natural diols and to their applications.

The apple is an agricultural product whose economic importance justifies the studies that are devoted to it. It is in fact a fruit of everyday consumption for the eating market but also an industrial fruit which is important to the food processing industry since it forms the basis of numerous products, such as fruit juices, fruit preparations intended for other industries, compotes and jams, or else drinks with a low alcohol level, such as traditional ciders.

Numerous studies have been devoted to the flavor of the apple, and have enabled more than 350 volatile compounds to be identified (Berger et al., 1988), including some which make an important contribution to the overall sensorial properties of the apple. Among such compounds, the C6 aldehydes such as cis-3-hexenal and trans-2-hexenal, the corresponding alcohols, certain esters, such as ethyl butyrate and ethyl 2-methylbutyrate, or β-damascenone, have an essential role (Belitz, 1992; Dürr et al., 1981).

In the course of these studies, the structure of two volatile compounds which are found in fairly significant amounts in certain varieties of apple has been elucidated, these being two homologous C8 diols: octane-1,3-diol and cis-oct-5-ene-1,3-diol, of formulae A and B:

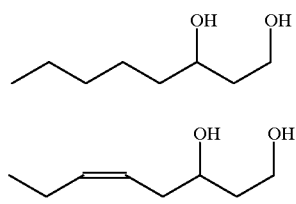

Figure 1A:
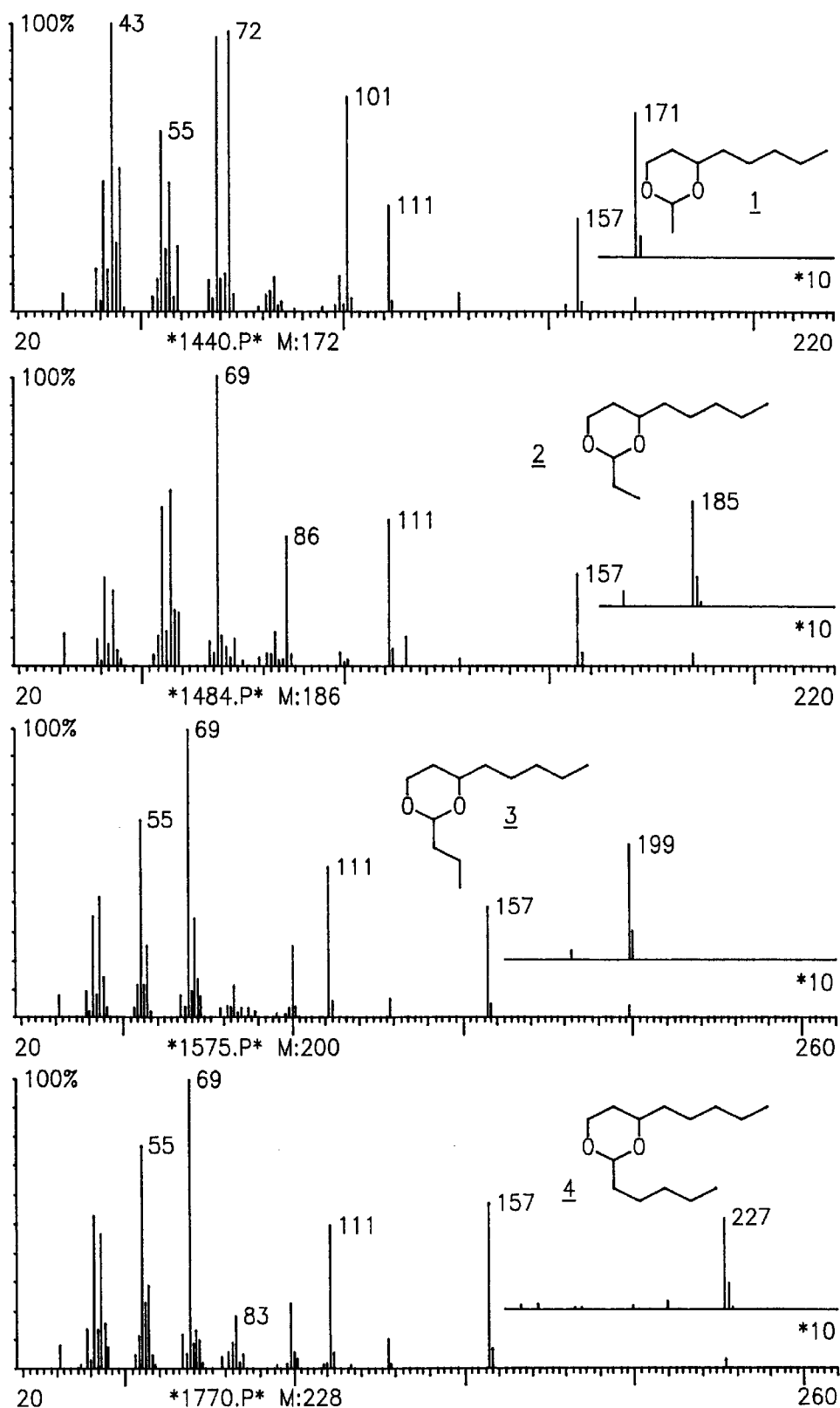
FIG. 1a shows the spectra of compound 1 to 4.

The first of these 1,3-diols was initially identified in a commercial fruit juice (Brulé et al., 1973) and has been found in highly variable amounts in various varieties of apple (Pyysalo et al., 1980), where it is accompanied by an unsaturated homolog—cis-oct-5-ene-1,3-diol—which is present in a much smaller amount (Yajima et al., 1984). Moreover, these β-glycols, whose absolute configuration is R (Schwab et al., 1989), are present in a not insignificant amount in the glycosylated bound form (Dettweiler et al., 1990; Schwab et al., 1989; Berger et al., 1988).

The Applicant has revealed that these 1,3-diols were derivatives that are essential to the synthesis of compounds with a 1,3-dioxane structure which have interesting aromatic properties, which the Applicant has identified in the natural state in extracts of apple or extracts of products derived from the apple. However, the fairly small amount of 1,3-diols present in apples made the synthesis of the compounds with a 1,3-dioxane structure of little interest from the industrial standpoint.

For this reason, the present invention relates to a method of biosynthesis of natural 1,3-diols of general formula I:

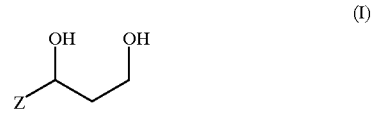

in which

Z is the pentyl group or the (Z)- or (E)-pent-2-enyl group, preferably the (Z) group, which consists in the conversion of a natural precursor of said 1,3-diols with the aid of an enzymatic complex and optionally separating the diols obtained.

In fact, it has been possible to reveal the fact that the use of a natural precursor of the 1,3-diols in question, namely, in particular, an unsaturated fatty acid such as linoleic acid, made it possible, under the action of an enzymatic complex, to obtain the above mentioned diols.

Preferably, the enzymatic complex originates from the apple, either by extraction and purification or, more simply, by adding linoleic acid to an apple mash and leaving the enzymatic system present therein to act.

As will be demonstrated in the text below, the proportions of the apple mash and of the precursor, especially linoleic acid, can vary to a fairly wide extent; in particular, the amount of precursor can reach 4% of the weight of apples employed, although it is preferred to use between 1 and 3% of the weight of apples.

The incubation time can depend on the type of apple used; however, incubation will last for from 15 minutes to 6 hours, and preferably from 3 hours to 5 hours.

The accompanying studies have shown that, among the apple mashes which are of particular interest, mention should be made of the mashes of a number of varieties of cider apples.

The tests which have been conducted, and which are described in the examples, show that by adding linoleic acid it is possible to multiply by 3 or 4 the amount of 1,3-diol present in the fruit.

The other conditions of the biosynthesis can be determined experimentally; preference will be given to operating the process at a temperature between 15 and 25° C. although, in certain cases, it is possible to employ different temperatures.

For economic reasons it is not particularly advantageous to separate the active enzymatic system, although it is possible to do so using the technologies which are well known in the art.

Finally, there is no need to employ special additives although it is possible, in certain cases, to envisage additives in order, for example, to stop the enzymatic reaction if necessary.

The 1,3-diols obtained can be separated by any known method for separating this type of diol, in particular by means of chromatographic systems or another purification method—over resin, for example.

As has been indicated above, these products are of particular interest for the synthesis of natural compounds having a 1,3-dioxane structure which were hitherto unknown and were identified for the first time by the applicant in the natural state in apple mashes and in extracts of products derived from the apple. Said compounds having a 1,3-dioxane structure, of general formula II

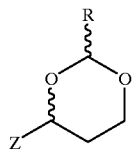
(II)

in which

Z is the pentyl or (Z)-pent-2-enyl group and R is a hydrocarbon group, preferably a $C_1$ to $C_6$ alkyl group, are obtained by spontaneous actualization of the corresponding natural 1,3-diol derivatives of general formula I, prepared by the method described above, with one or more natural aldehydes of formula

The method of spontaneous actualization is preferably conducted with a desiccant such as anhydrous silica.

In order to carry out this actualization preference will be given to the use of natural aldehydes, especially $C_1$ to $C_6$ aliphatic aldehydes or aromatic aldehydes, namely those in which the radical R is, in particular, a $C_1$ to $C_6$ alkyl radical and/or an aromatic radical, especially the phenyl radical; preferably, the aldehydes in question will be selected from ethanal, propanal, butanal and hexanal.

The natural 1,3-diols will be placed in the presence of a stoichiometric amount of aldehyde.

The reaction is conducted for a period of from 12 hours to 3 days, preferably from 24 to 48 hours, at a temperature of the order of from 10 to 40° C.

The natural compounds having a 1,3-dioxane structure that are obtained are purified by distillation or chromatography on a silica column and can be analyzed by gas chromatography. When they include stereoisomers, the latter can be separated by any appropriate method, in particular by gas chromatography and, especially, on a chiral column.

As will be indicated below, the compounds having a 1,3-dioxane structure exhibit notes which are of interest from the aromatic standpoint.

For this reason, the present invention also relates to compositions comprising these dioxanes and, more particularly, the following derivatives:

Structure of the 1,3-dioxanes Formed from the 1,3-diols (compounds A and B) and the Aldehydes Ethanal, Propanal, Butanal, Hexanal

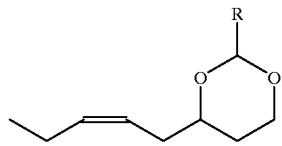

4-pentyl-1,3-dioxane derivatives:

1: R=methyl: 2-methyl-4-pentyl-1,3-dioxane
2: R=ethyl: 2-ethyl-4-pentyl-1,3-dioxane
3: R=propyl: 2-propyl-4-pentyl-1,3-dioxane
4: R=pentyl: 2-pentyl-4-pentyl-1,3-dioxane

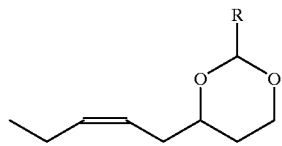

[4-(Z)-pent-2-enyl]-1,3-dioxane derivatives:

5: R=methyl: 2-methyl[4-(Z)-pent-2-enyl]-1,3-dioxane
6: R=ethyl: 2-ethyl[4-(Z)-pent-2-enyl]-1,3-dioxane
7: R=propyl: 2-propyl[4-(Z)-pent-2-enyl]-1,3-dioxane
8: R=pentyl: 2-pentyl[4-(Z)-pent-2-enyl]-1,3-dioxane.

The natural compounds having a 1,3-dioxane structure that are obtained in this way possess analytical features which enable their natural or synthetic origin to be revealed.

Analysis by gas chromatography on a chiral column of the saturated and unsaturated 1,3-diols and of the 1,3-dioxanes (compounds 1 to 8) which are their precursors makes it possible to distinguish the products of natural origin from the products obtained by the route of chemical synthesis.

The process for preparing the natural compounds having a 1,3-dioxane structure according to the invention allows access to a new class of aromatizing molecules which possess green, fresh and fruity notes. The present invention also relates to any aromatic composition or perfumery composition which comprises these natural compounds having a 1,3-dioxane structure.

The examples below will enable other advantages and features of the present invention to be revealed.

Example 1

Determination of the Octane-1,3-diol and Cis-oct-5-ene-1,3-diol Content in the Apple 100 g of cider apples are mashed in the presence of 100 ml of water. The mash is subsequently extracted with dichloromethane following the addition of an internal standard (methyl undecanoate). The extract is subsequently concentrated to 1 ml and is analyzed by gas chromatography.

The conditions of gas-chromatographic analysis are as follows:

FFAP column (Hewlett Packard); 60 m; internal diameter: 0.32 mm; thickness of the film: 0.53 µm;

chiral column;

Hewlett Packard 6890 chromatograph;

temperature and flow rate regime: isothermal at 60° C., 3 min; 3° C./min to 120°; 2° C./min to 220 C.; isothermal at 220° C., 60 min; carrier gas: helium at 2 ml/min, kept constant by means of an electronic pressure regulator; FID detector: hydrogen: 30 ml/min.

The contents of 1,3-diols of formulae A and B vary greatly from one variety of apple to another. For this reason, the Applicant has carried out research into which varieties of apple were the richest in compounds A and B, in order to optimize the method of preparation according to the invention.

The content of 1,3-diols, both free and bound in the form of glucosides, of various varieties of apple was determined by adding 5% by weight of a commercial enzymatic preparation Rohapect B1L (Rhom), Novozym (Novo) or PLM (Grindsted) relative to the amount of apples employed. This commercial enzymatic preparation contains both a pectinase activity and a glucosidase activity. The enzyme homogenate is kept at 30° C. with stirring for 24 hours before extraction.

Large amounts of these 1,3-diols have been found, especially in certain varieties of cider apple, which had not been reported in the literature until now.

The content of 1,3-diols in two varieties of cider apple was determined at different stages of maturity of the fruit, thereby showing that the amount of 1,3-diols increases considerably when the fruit ripens. In accordance with what was already known, and as shown by the study carried out on these two varieties of cider apple (Table 1), a major proportion of the two 1,3-diols is present in the fruit in the non-volatile state, bound in the form of glucosides. The study was carried out on fruit picked in October, analyzed and then stored and sampled at one-month intervals during November and December (stages 1, 2 and 3):

TABLE 1

Content of 1,3-diols of formulae A and B in two varieties of cider apple at different stages of maturity

| | Octane-1,3-diol | | Oct-5-ene-1,3-diol | |
|---|---|---|---|---|
| | free | bound | free | bound |
| Cider apple variety 1 (mg/kg) | | | | |
| Frozen fruits | 531 | 81 | 49 | 13 |
| Stage 1 | 23 | | 20 | |
| Stage 2 | 152 | — | 46 | — |
| Stage 3 | 819 | 406 | 106 | 46 |
| Cider apple variety 2 (mg/kg) | | | | |
| Frozen fruits | 265 | 195 | 28 | 28 |
| Stage 1 | 22 | — | 12 | — |

TABLE 1-continued

Content of 1,3-diols of formulae A and B in two varieties of cider apple at different stages of maturity

| | Octane-1,3-diol | | Oct-5-ene-1,3-diol | |
|---|---|---|---|---|
| | free | bound | free | bound |
| Stage 2 | 125 | — | 22 | — |
| Stage 3 | 247 | 74 | 28 | 12 |

Example 2

Stimulation of Enzymatic Activity for the Purpose of Producing Natural 1,3-diols The activity of the enzymatic systems involved in the biosynthesis of the 1,3-diols of formulae A and B depends not only on the variety of apple but also on the amount of natural precursor available.

In fact, as shown by the results obtained in Table 2, only the cider apples possess sufficient enzymatic activity to produce large amounts of 1,3-diols in the presence of linoleic acid as precursor.

By contrast, three varieties of table apples which were studied have an enzymatic activity which is very low or zero and does not permit the biosynthesis of the two 1,3-diols of formulae A and B from linoleic acid.

TABLE 2

Production of the two 1,3-diols of formulae A and B, depending on the variety of apple, in the presence of linoleic acid as natural precursor

| Variety | Octane-1,3-diol (g/kg of apple) | Oct-5-ene-1,3-diol (g/kg of apple) |
|---|---|---|
| Cider apple variety 1 | 5.10 | 0.150 |
| Cider apple variety 2 | 2.50 | 0.037 |
| Table apple variety 1 | 0.020 | 0.008 |
| Table apple variety 2 | 0 | 0 |
| Table apple variety 3 | 0.006 | 0.003 |

The activity of the enzymatic systems also depends on the amount of natural precursor available.

The activity of the enzymatic systems may therefore be stimulated by adding their natural precursor, which in this case is a fatty acid precursor.

Since one of the major fatty acids of the apple is linoleic acid, it was the latter which was added, initially, to a mash of a variety of cider apples, in varying amounts.

100 g of cider apples of variety 1 are mashed in the presence of 150 ml of water and 2 g of pure linoleic acid or of linoleic acid in the form of linseed oil hydrolyzate. After 4 hours of incubation at room temperature and with stirring, the homogenate is extracted with the solvent following addition of an internal standard as in Example 1.

The optimum amount of linoleic acid required for the formation of the 1,3-diols of formulae A and B was therefore determined by measuring the amount of 1,3-diols formed in cider apple homogenates containing increasing amounts of fatty acid.

The content of the two 1,3-diols is determined by gas chromatography (GC) following extraction and concentration of the extract. The results obtained are indicated in Table 3.

TABLE 3

Determination of the optimum amount of linoleic acid required for the biosynthesis of the natural 1,3-diols of formulae A and B in a cider apple of variety 1

| Linoleic acid added (g/kg of apple) | Octane-1,3-diol (g/kg of apple) | Oct-5-ene-1,3-diol (g/kg of apple) |
|---|---|---|
| 0 (control) | 1.05 | 0.033 |
| 10 | 2.40 | 0.094 |
| 15 | 3.80 | 0.124 |
| 20 | 4.17 | 0.127 |
| 25 | 3.30 | 0.098 |
| 30 | 2.70 | 0.092 |
| 40 | 2.50 | 0.077 |

The maximum level of production of the two 1,3-diols is attained for an amount of linoleic acid of 2% relative to the weight of cider apples of variety 1 employed. The addition of large amounts of fatty acid precursor results in a substantial decrease in the amount of 1,3-diols produced, very probably as a result of inhibition of the enzymatic systems by the substrate.

Since the optimum amount of linoleic acid required for the formation of the 1,3-diols is 2% relative to the weight of cider apples of variety 1 employed, the optimum incubation time in an apple homogenate was then determined (Table 4) using this amount of precursor.

TABLE 4

Kinetics of formation of the two natural 1,3-diols of formulae A and B in a mash of cider apples of variety 1

| Time | Octane-1,3-diol (g/kg of apple) | Oct-5-ene-1,3-diol (g/kg of apple) |
|---|---|---|
| T0 (control) | 1.13 | 0.033 |
| T + 5 min | 1.60 | 0.044 |
| T + 10 min | 2.15 | 0.058 |
| T + 15 min | 3.30 | 0.096 |
| T + 30 min | 4.00 | 0.130 |
| T + 60 min | 4.10 | 0.135 |
| T + 150 min | 4.45 | 0.140 |
| T + 240 min | 4.75 | 0.160 |
| T + 360 min | 4.75 | 0.140 |

From the kinetics above it is evident that the maximum amount of the natural 1,3-diols of formulae A and B is obtained after 4 hour s of incubation in the presence of linoleic acid as precursor. At that point the content of octane-1,3-diol is increased by a factor of approximately three. Similarly, the content of oct-5-ene-1,3-diol incr eases in the same proportions, thereby revealing that linoleic acid is the origin of these compounds by means of a metabolic route, at present unknown, but probably involving enzymes of the lipoxygenase type which are specific to the apple.

Example 3

Preparation of Natural Compounds Having a 1,3-dioxane Structure (compounds 1 to 8)

The totality of these compounds (1 to 8), which are important from a sensorial standpoint, are obtained in the natural state by spontaneous reaction of the corresponding aldehydes and homologous 1,3-diols isolated from the apple by the following method:

The 1,3-diols are placed in the presence of a stoichiometric amount of aldehyde (ethanal, propanal, butanal or hexanal) and anhydrous silica with stirring at room temperature for 48 hours.

The reaction medium is subsequently analyzed by GC and the compounds of the 1,3-dioxane structure are assayed. The yields obtained for compounds 1 to 4 are as follows (Table 5). The mass spectra of compounds 1 to 4 are shown in FIG. 1a.

TABLE 5

| Octane-1,3-diol (MW = 146) Number of moles | Aldehyde | Aldehyde Number of moles | 4-Pentyl-1,3-dioxane derivatives | | |
|---|---|---|---|---|---|
| | | | Compound having a 1,3-dioxane structure that is obtained | Number of moles | Yield obtained |
| 0.01028 | ethanal (MW = 44) | 0.01805 | 1 | 0.00740 | 72.0% |
| 0.00693 | propanal (MW = 58) | 0.01118 | 2 | 0.00158 | 22.8% |
| 0.00729 | butanal (MW = 72) | 0.00904 | 3 | 0.00135 | 18.5% |
| 0.00718 | hexanal (MW = 100) | 0.00894 | 4 | 0.00078 | 10.8% |

It was not possible to calculate the yields obtained for compounds 5 to 8.

The synthesis of the unsaturated compounds having a 1,3-dioxane structure (5 to 8) can be carried out chemically starting from oct-5-ene-1,3-diol, isolated beforehand from a cider apple homogenate treated by the method of the invention, and natural aldehydes ethanal, propanal, butanal and hexanal in the presence of a catalytic amount of acid.

Figure 1B:
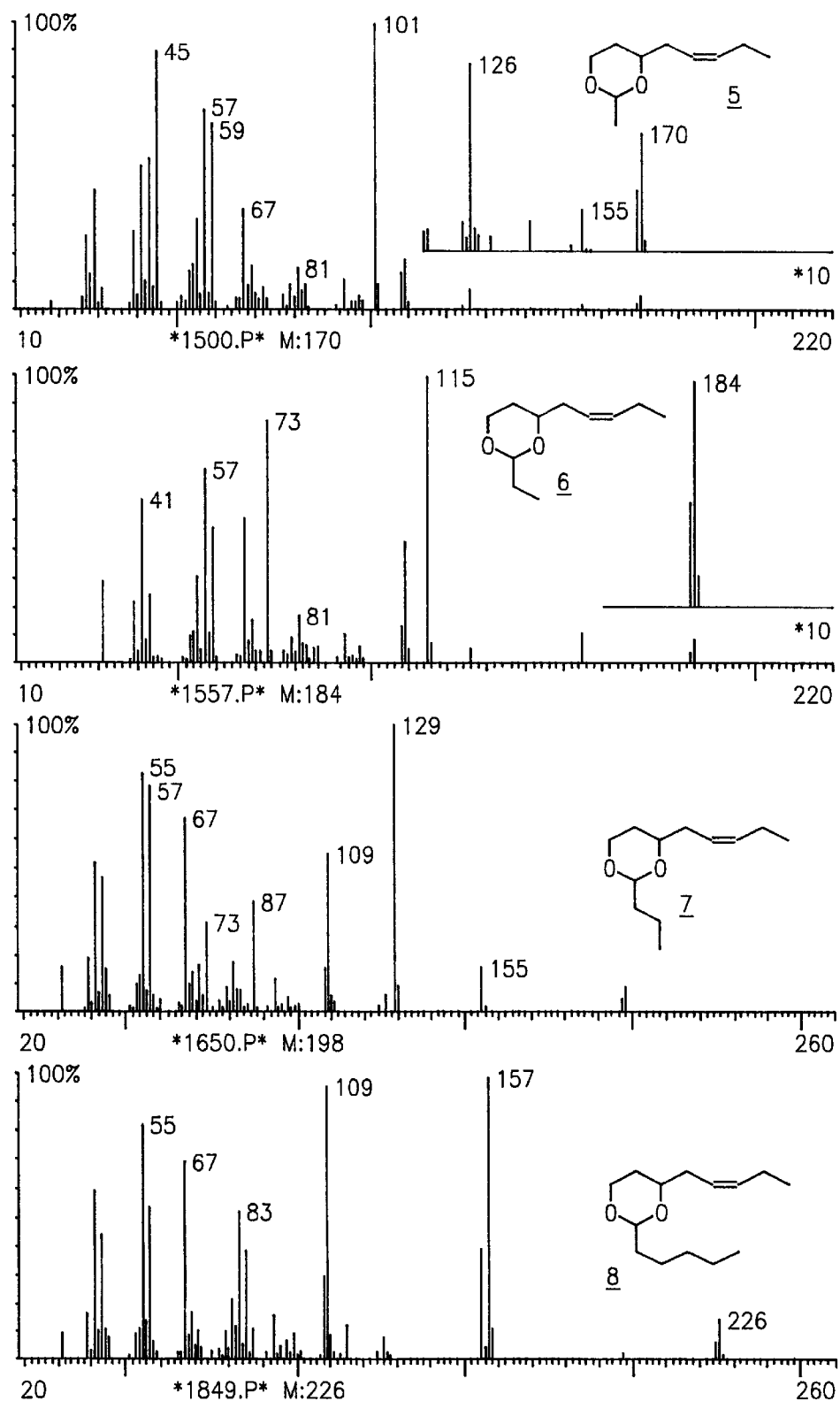
FIG. 1b shows the nass spectra of compound 5 to 8.

Therefore, and as analytical references, the mass spectra of the four compounds having a 1,3-dioxane structure and possessing an unsaturated side chain (compounds 5 to 8) obtained by chemical synthesis are shown in FIG. 1b.

The conditions of analysis by GC/MS coupling utilize the same chromatographic conditions as described in Example 1 and a Profile (Kratos) magnetic sector mass spectrometer operated in EI mode; ionization energy: 70 ev [sic], vacuum $2.10^{-5}$ torr; source temperature: 150° C.; interface temperature: 240° C.

The compounds 1 to 8 obtained can be analyzed by GC/olfactometry and the sensorial characteristics of each of them can therefore be evaluated (Table 6).

TABLE 6

| Compound | 4-Pentyl-1,3-dioxane derivatives | Compound | [4-(Z)-(Pent-2-enyl)]-1,3-dioxane derivatives |
|---|---|---|---|
| 1 | Very green, powerful, pleasant | 5 | green, sharp, aggressive, moldy, fairly weak |
| 2 | Fruity, orange, flowery, fresh, very sharp | 6 | fruity, sharp, less fresh, powdered apple, weak |
| 3 | Fruity, sharp, weak, slightly burnt | 7 | very fruity, powerful |
| 4 | Green, dry grass, slightly fruity, weak | 8 | dry grass, very weak |

Example 4

Isolation and Identification of Enantiomers of the Natural Compounds Having a 1,3-dioxane Structure Octane-1,3-diol and oct-5-ene-1,3-diol possess an asymmetric carbon, which leads to the possibility of optical isomerism. The enantiomers of these compounds, when they are present, can be separated by gas chromatography on a chiral column, thereby permitting the revelation of the origin of the 1,3-diols—the compounds obtained by synthesis being racemic whereas the diols extracted from the apple are enantiomeric ally pure.

In the course of the reaction of the 1,3-diols with the aldehydes from the apple (ethanal, propanal, butanal and hexanal), which leads to the formation of the dioxanes 1 to 8, an additional asymmetric carbon is introduced, resulting in the presence of diastereoisomer which can be separated by gas chromatography on a normal column. One of the diastereoisomer is greatly in the majority. Analysis on a chiral column of these compounds enables the enantiomers of each of the diastereoisomer to be separated. This analysis makes it possible to distinguish the compounds 1 to 8 as a function of their origin, natural or synthetic.

The stereoisomerism of the compounds having a 1,3-dioxane structure (compounds 1 to 8) is influenced by the length of the side chain carried by the 1,3-dioxane nucleus.

The conditions of gas-chromatographic analysis are the same as in Example 1.

What is claimed is:

1. A method of synthesis of at least one natural 1,3-diol derivative of general formula:

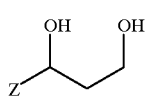

(I)

in which

Z is the pentyl group or the (Z)- or (E)-pent-2-enyl group, which consists in enzymatically converting an unsaturated fatty acid precursor of said diol, which is the same as that which is naturally present in a cider apple, with the aid of an enzymatic complex which exhibits the same activity as that which is present in a cider apple or which consists in adding said precursor to cider apple mash, thus permitting the enzymatic complex naturally present in cider apple mash to enzymatically convert said precursor to said diol.

2. The method according to claim 1, wherein the unsaturated fatty acid is linoleic acid.

3. The method according to claim 1, wherein the enzymatic complex is that which is in the apple mash.

4. The method according to claim 2, wherein the linoleic acid is added to the apple mash in a proportion up to 4% of the weight of apple employed.

5. The method according to claim 4, wherein the proportion of linoleic acid added to the apple mash is between 1 and 3% of the weight of apples employed.

6. The method according to claim 2, wherein the incubation time of the apple mash/linoleic acid mixture is between 15 minutes and 6 hours.

7. The method according to claim 6, wherein the incubation time of the apple mash/linoleic acid mixture is between 3 and 5 hours.

8. The method according to claim 1, wherein the natural 1,3-diol derivative of general formula I is isolated from the apple mash by absorption on resin.

9. A Method of preparing at least one natural compound having a 1,3-dioxane structure, of general formula II:

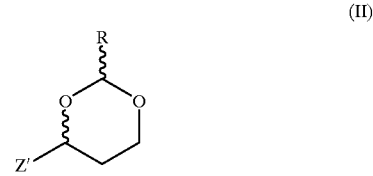

(II)

in which

Z' is the pentyl or (Z)-pent-2-enyl group and R is a hydrocarbon group, comprising spontaneously acetalizing a corresponding natural 1,3-diol derivative, the corresponding natural 1,3-diol derivative being prepared by the method of synthesis of at least one natural 1,3-diol derivative of general formula I:

(I)

in which

Z is the pentyl group or the (Z)- or (B)-pent-2-enyl group, which consists in enzymatically converting an unsaturated fatty acid precursor of said diol which is naturally present in a cider apple with the aid of an enzymatic complex which is extracted from a cider apple or which consists in adding said precursor to a cider apple mash thus permitting the enzymatic complex naturally present therein to enzymatically convert said precursor to said diol, with one or more natural aldehydes of formula

10. The method according to claim 9, wherein the natural 1,3-diol derivatives of general formula I are placed in the presence of a stoichiometric amount of at least one natural aldehyde and a desiccant.

11. The method according to claim 9, wherein the natural aldehyde is at least one $C_1$–$C_6$ aliphatic or at least one aromatic.

12. The method according to claim 11, wherein the natural aldehyde is ethanal, propanal, butanal or hexanal.

13. The method according to claim 9, wherein the actualization is conducted with stirring for from approximately 24 to 48 hours at a temperature of between 10 and 40° C.

14. The method according to claim 9, wherein the natural compound having a 1,3-dioxane structure, of general formula II is purified by distillation or chromatography on a silica column.

15. The method according to claim 14, wherein each natural compound having a 1,3-dioxane structure, of general formula II obtained in the form of a mixture of diastereoisomer is analyzed by gas chromatography on a chiral column in order to separate its enantiomers.

16. The method according to claim 1, wherein Z is the (Z)-pent-2-enyl group.

17. The method according to claim 10, wherein the desiccant is anhydrous silica.

18. A method of synthesis of at least one natural 1,3-diol derivative of general formula:

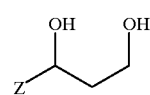

(I)

in which

Z is the pentyl group or the (Z)- or (E)-pent-2-enyl group, which comprises mashing a cider apple in the presence of an unsaturated fatty acid precursor of said diol which is naturally present in the cider apple to enzymatically convert said precursor to said diol.

19. The method according to claim 18, wherein the natural unsaturated fatty acid precursor is linoleic acid.

20. The method according to claim 19, wherein the linoleic acid is added to the apple mash in proportions up to 4% of the weight of cider apple employed.

21. The method according to claim 20, wherein the proportion of linoleic acid added to the apple mash is between 1 and 3% of the weight of apples employed.

22. The method according to claim 19, wherein the incubation time of the apple mash/linoleic acid mixture is between 15 minutes and 6 hours.

23. The method according to claim 22, wherein the incubation time of the apple mash/linoleic acid mixture is between 3 and 5 hours.

24. The method according to claim 18, wherein the natural 1,3-diol derivatives of general formula I are isolated from the apple mash by absorption on resin.

* * * * *

UNITED STATES PATENT AND TRADEMARK OFFICE
CERTIFICATE OF CORRECTION

PATENT NO.   : 6,384,243 B1
DATED        : May 7, 2002
INVENTOR(S)  : Pascal Marc Brunerie It is certified that error appears in the above-identified patent and that said Letters Patent is hereby corrected as shown below:

Column 1,
Line 39, immediately below formula (A), insert -- octane-1,3-diol --;
Line 45, immediately below formula (B), insert -- cis-oct-5-ene-1,3-diol --.

Column 3,
Lines 26, 37 and 39, "actualization" (each occurrence) should read -- acetalization --.

Column 10,
Line 57, "(B)" should read -- (E) --.

Signed and Sealed this

Twentieth Day of January, 2004

JON W. DUDAS
*Acting Director of the United States Patent and Trademark Office*